(12) United States Patent
Saxler et al.

(10) Patent No.: US 8,518,068 B2
(45) Date of Patent: Aug. 27, 2013

(54) SCALPEL, IN PARTICULAR FOR OPHTHALMOLOGIC APPLICATIONS

(75) Inventors: Wilfried Saxler, Brühl (DE); Benedikt Thimm, Köln (DE)

(73) Assignee: Rheinische Fachhochschule Köln gGmbH, Köln (DE)

( * ) Notice: Subject to any disclaimer, the term of this patent is extended or adjusted under 35 U.S.C. 154(b) by 0 days.

(21) Appl. No.: 13/321,446

(22) PCT Filed: Jun. 23, 2010

(86) PCT No.: PCT/EP2010/058896
§ 371 (c)(1),
(2), (4) Date: Nov. 18, 2011

(87) PCT Pub. No.: WO2011/000752
PCT Pub. Date: Jan. 6, 2011

(65) Prior Publication Data
US 2012/0089165 A1    Apr. 12, 2012

(30) Foreign Application Priority Data
Jun. 29, 2009 (DE) .......................... 10 2009 030 874

(51) Int. Cl.
*A61B 17/32* (2006.01)
(52) U.S. Cl.
USPC ........................................... 606/170; 30/151
(58) Field of Classification Search
USPC ................. 606/107, 166, 170; 30/151, 329
See application file for complete search history.

(56) References Cited

U.S. PATENT DOCUMENTS

| 3,325,900 A | 6/1967 | Sohlberg |
| 5,098,438 A | 3/1992 | Siepser |

(Continued)

FOREIGN PATENT DOCUMENTS

| DE | 196 52 098 A1 | 6/1998 |
| DE | 299 19 917 U1 | 1/2000 |

OTHER PUBLICATIONS

International Search Report for PCT/EP2010/058896 dated Oct. 4, 2010.

(Continued)

*Primary Examiner* — Victor Nguyen
(74) *Attorney, Agent, or Firm* — Marshall, Gerstein & Borun LLP

(57) ABSTRACT

A scalpel, in particular for ophthalmologic applications, having a handle head and a blade, wherein the blade, which includes a blade shank and a blade face, is inserted into a handle head of the handle, and at least one cutting edge is formed on the blade face, wherein the blade shank is configured together with the blade face as a body on which a continuous smooth rear surface is formed, whereby the front of the body opposite from the rear surface forms a cylindrical surface in the area of the blade shank and forms the top of the blade in the area of the blade face, and the end of the handle head has two surfaces that are slanted with respect to each other and that abut, like a roof edge, in an edge that is perpendicular to the axis of the handle, and whereby, in a first of the slanted surfaces, there is an opening for inserting the blade, whereby the inserted blade comes to lie in the opening in such a way that the smooth rear surface is flush with the first slanted surface.

11 Claims, 2 Drawing Sheets

(56) References Cited

U.S. PATENT DOCUMENTS

| | | | |
|---|---|---|---|
| 5,718,708 | A | 2/1998 | Webb |
| 7,022,128 | B2 * | 4/2006 | Morawski et al. ............ 606/167 |
| 2004/0182823 | A1 | 9/2004 | Rodgers et al. |
| 2004/0215174 | A1 | 10/2004 | Morawski et al. |
| 2005/0245953 | A1 | 11/2005 | Cote |

OTHER PUBLICATIONS

International Preliminary Report on Patentability for Application No. PCT/EP2010/058896, dated Jan. 17, 2012.

* cited by examiner

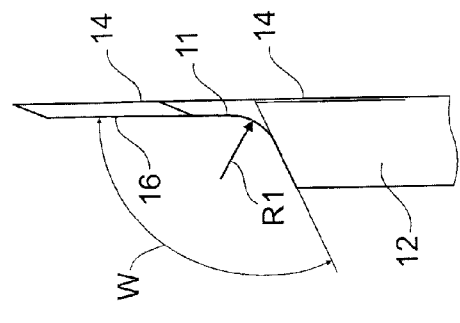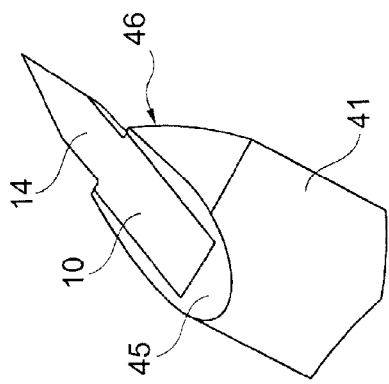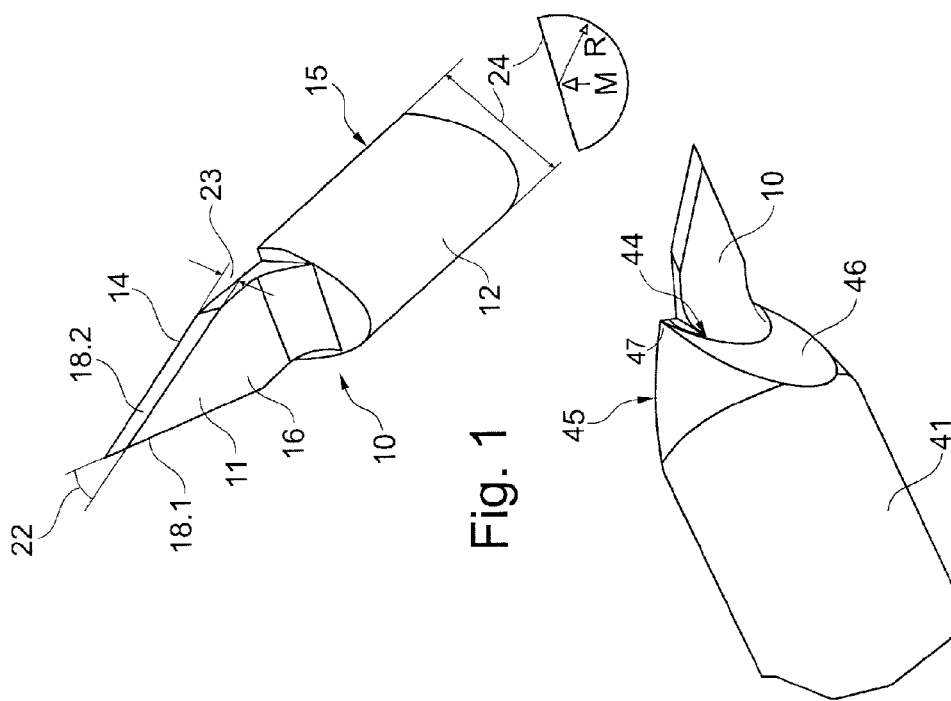

SCALPEL, IN PARTICULAR FOR OPHTHALMOLOGIC APPLICATIONS

BACKGROUND OF THE INVENTION

1. Field of the Invention

The invention relates to a scalpel, in particular for ophthalmologic applications.

2. Related Technology

German patent specification DE 19652098 C2 discloses a surgical instrument that is entirely (that is to say, the handle and the blade) made of ceramic material and that is produced by an injection molding process. Another scalpel consists of a blade made of ceramic with a cutting edge and a handle, whereby the handle is permanently inserted into the distal end of a shank made of stainless steel (German utility model DE 29919914 U1). Such scalpels are usually made for one-time use.

U.S. Pat. No. 5,718,708 A discloses an ophthalmologic instrument that is configured as a scooping and scraping tool. The tool has an obtuse-angled head with three cutting edges arranged on the side. The front part of the tool head is bent at a small angle relative to the middle part. The bottom of the bent part has a rough structure for scraping purposes. This instrument cannot be used for flat incisions or flat puncturing during cataract surgery. A scalpel designed for flat incisions or flat puncturing is described in U.S. Pat. No. 5,098,438 A.

U.S. Pat. No. 3,325,900 A shows a scalpel consisting of a metal handle and a metal tool head. A blade holder into which metal blades with one or two cutting edges can be inserted is configured in the tool head.

Another surgical instrument is known that is fitted with a guard that can be slid towards the tip of the scalpel (U.S. patent application 2004/0215174 A1). This instrument is a high-tech tool and thus has a complex design, consisting of a plurality of individual parts. The scalpel blade is detachably affixed so that it can be replaced once it is worn out.

SUMMARY OF THE INVENTION

The invention is based on the objective of putting forward an inexpensive scalpel that is simply structured and that can be used multiple times, particularly for ophthalmologic applications in which especially flat incisions or flat puncturing motions can be made.

Accordingly, the invention provides a scalpel, in particular for ophthalmologic applications, comprising a handle head and a blade, wherein the blade, which includes a blade shank and a blade face, is inserted into a handle head of the handle, and at least one cutting edge is formed on the blade face, wherein the blade shank is configured together with the blade face as a body on which a continuous smooth rear surface is formed, whereby the front of the body opposite from the rear surface forms a cylindrical surface in the area of the blade shank and forms the top of the blade in the area of the blade face, and the end of the handle head has two surfaces that are slanted with respect to each other and that about, like a roof edge, in an edge that is perpendicular to the axis of the handle, and whereby, in a first of the slanted surfaces, there is an opening for inserting the blade, whereby the inserted blade comes to lie in the opening in such a way that the smooth rear surface is flush with the first slanted surface.

The essence of the invention is that two surfaces that are slanted like a wedge or like a roof edge with respect to each other are formed on the handle head and, in a first of the slanted surfaces, there is an opening for inserting the blade, whereby the inserted blade comes to lie in the opening in such a way that the rear surface of the body consisting of the blade shank and the blade face is flush with the first slanted surface.

Thanks to the flush arrangement of the rear surface with the first slanted surface, flat incisions or flat puncturing motions can be made on the cornea of the eye, something that is especially necessary during surgery to the lens of the eye.

Additional preferred embodiments and augmentations are elaborated upon below, whereby the features can be implemented individually or together with each other.

The opening (bore) in the handle head is configured to match the cross section of the blade shank. This means that the cross section of the opening is adapted to the configuration of the blade shank.

Preferably, the blade shank is configured as a body that is a cylinder that is bisected parallel to the longitudinal axis, whereby the intersecting plane of the body is in the longitudinal axis of the cylinder (cylinder axis). The rear surface corresponds to the plane of half of the cylinder. A (semi-)cylindrical configuration allows a precise centering of the blade in the handle. Moreover, the insertion of the blade shank and the fastening (in an adhesive process) are simplified since the adhesive is distributed uniformly on the cylindrical surface; no corners are formed.

An essential aspect is that the length of the blade is dimensioned in such a way that the blade remains within an imaginary envelope that extends beyond the end of the handle head. Consequently, there is no place where the length of the blade projects beyond the (imaginary) envelope that extends beyond the end of the handle head. This has the advantage that the blade of a scalpel lying on a tray does not touch the substrate. This prevents contamination or damage due to contact with the substrate.

The first slanted surface on the handle head should be slanted by an angle between 25° and 35°, preferably by an angle of 30°, relative to the longitudinal axis of the handle.

The "normal version" of the scalpel has two cutting edges on the blade. In such a version, the two cutting edges of the blade converge in the form of an equilateral triangle symmetrically relative to the longitudinal axis of the blade. In the symmetrical version, the shape of the equilateral triangle would taper at an angle of 45°.

The cutting edges of the blade are beveled from the rear surface towards the top of the blade. In particular, two versions have been studied. In the first one, the cutting edge angle is about 45°; in a second blade shape, the angle has a value of about 30°. The configurations are explained in greater detail in the figure description.

A cutting edge angle of about 45° is created for blades that are of a certain thickness. A very flat configuration of the blade results if the cutting edge angle is reduced, for example, to 30°. The top and the rear of the blade are no longer parallel. In this configuration, the blade does not have a constant cutting thickness since the edges on the blades converge and form a shared 'middle line' in the middle of the blade (see FIG. 6).

The blade is made of ceramic (zirconium oxide, aluminum oxide, or mixed-oxide ceramic) and can be worked by means of grinding and polishing processes. Zirconium oxide has proven to be especially suitable. The ceramic starting material is treated in a HIP (hot isostatic pressing) process and is then free of pores, as a result of which it can be sterilized very well. Scalpels made of zirconium oxide combine great hardness and wear resistance with low sensitivity to impact.

Other blade materials are, of course, equally well-suited for the production of scalpels, whereby diamond is also an option. Thanks to its great hardness and the resultant wear resistance, diamond can be used multiple times. However, diamond is very sensitive to impact and also very expensive.

Metal blades are only somewhat suitable since they cannot be used more than once.

The shank of the blade is permanently glued into the handle head. Since the blade shank fits tightly into the opening in the handle head, one drop of superglue is sufficient to ensure the fit and the firmness. A scalpel made in this manner can be sterilized several times, thus allowing multiple use.

The diameter of the (semi-)cylindrical blade shank is, for example, 4 mm. The thickness of the cutting edge: 0.2 mm to 0.3 mm; the cutting edges are beveled relative to the rear surface at an angle of about 45°. When very accurate grinding machines are used, the result is surfaces with a high level of smoothness, so that the surfaces do not have to be further polished. However, the grinding process can be followed by a polishing step for the cutting surfaces using diamond grinding disks with a grain in the μm range.

The present invention is not limited to the embodiments described above, but rather, also encompasses all of the embodiments involving the same effect as set forth in the invention. Scalpels with only one cutting edge on the blade should likewise be included. Moreover, the invention can fundamentally also be used for all microsurgical scalpels.

BRIEF DESCRIPTION OF THE DRAWINGS

Additional details and advantages of the invention are explained on the basis of figures. In detail, they show the following:

FIG. 1: a perspective view of a first blade;
FIG. 2: a side view of a blade;
FIG. 3: a first perspective view of a blade in the handle head;
FIG. 4: a second perspective view of a blade in the handle head.

DETAILED DESCRIPTION

Figure 5:
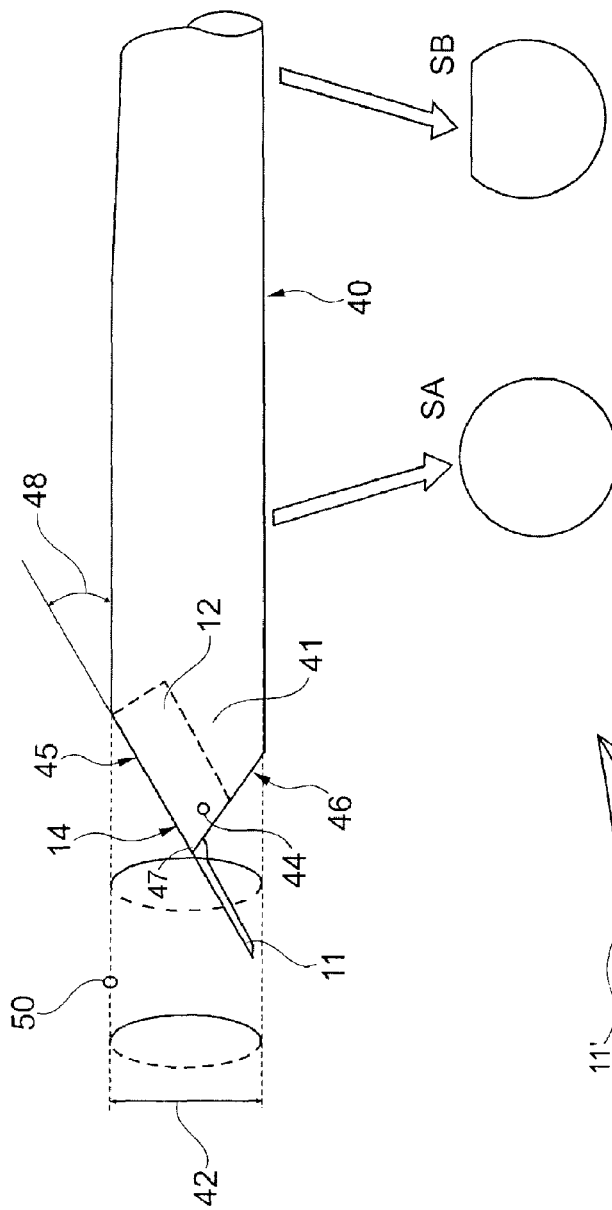
FIG. 5: a side view of the blade in the handle head.

FIG. 1 shows a perspective view and FIG. 2 shows a side view of a blade 12 having a blade shank 12 and a blade face 11 with two cutting edges 18.1, 18.2. The two cutting edges of the blade converge in the form of an equilateral triangle symmetrically relative to the longitudinal axis of the blade and they taper at an angle 22 of 45°. The cutting edges 18.1, 18.2 are beveled from the rear surface 14 towards the front (towards the top 16 of the blade). The blade shank 12 and the blade face 11 together form the body. The body has a continuous smooth rear surface 14, running from the tip of the blade face to the end of the blade shank. The blade shank with a cylindrical surface and the blade face with its blade top 16 are formed opposite from the rear surface.

The top 16 of the blade 11—in the embodiment shown in FIG. 1—is parallel to the rear 14 of the blade. The blade shank 12 is configured as a cylinder that is bisected along its longitudinal axis and that has a radius R (or with a cylinder diameter 24). The cylinder axis (reference numeral M) is in the intersecting plane.

The rear surface 14 is in the plane of the bisected cylinder. The rear 15 of the blade shaft and the rear 14 of the blade together form a shared plane. The semi-cylindrical configuration allows a precise centering of the blade in the handle 40 (see FIGS. 3 and 4). The surfaces of the blade 10 are made by grinding ceramic material, as a result of which—as a function of the contour of the grinding disks—rounded areas are formed, for example, a transition from the blade shank to the blade, which runs at an obtuse angle W in FIGS. 1 and 2. The apex of the transition—according to FIG. 2—has a rounded area with a radius R1. The rounded areas present at the transition from the blade to the shank have a radius that is determined by the configuration of the grinding disk employed. Rounded areas with radii in the range of about 1 mm are practical in order to minimize notch stresses at the transition.

FIGS. 3 and 4 show the handle head 41 on which two surfaces 45, 46 are formed that are slanted like a wedge or like a roof edge with respect to each other. The surfaces 45, 46 abut, like a roof edge, in an edge (47) that is perpendicular to the axis of the handle. The first slanted surface 45 has an opening 44 (see FIG. 5) into which the blade shank 12 can be inserted. In particular, FIG. 4 shows that the inserted blade 10 comes to lie in the opening 44 in such a way that the rear surface 14 is flush with the first slanted surface 45.

In ophthalmologic surgical procedures, especially in a so-called tunnel incision on the lens of the eye, the scalpel according to the invention is held in such a way that the rear surface comes to lie approximately parallel (or slightly slanted) with respect to the cornea. The tip of the blade can then be inserted and pushed forward in its full length into the cornea without the handle head detrimentally touching the cornea.

FIG. 5 shows a side view of the handle 40 at its front end. The blade 10 has been permanently glued into the opening 44, which has the shape of the blade shank 12 (semi-cylindrical according to FIG. 1). The length of the blade 10 is dimensioned in such a way that the blade 70, or to put it more precisely, the tip of blade, remains within an imaginary envelope 50 that extends beyond the end of the handle head 41. The rear surface 14 is slanted relative to the axis of the handle at an angle 48. The angle 48 can be between 25° and 35°, preferably it should be 30°.

The following can be given as typical dimensions of the handle: length of the handle: 130 mm and diameter 42 of the handle at the handle head 41: 7 mm to 8 mm. At the handle head, the handle has a cylindrical configuration, which is indicated by the section SA in FIG. 5. Towards the end of the handle, there is a slight flattening of the cylinder, which has the advantage that the scalpel rolls into a defined position when it is placed onto a substrate. The flattening of the handle changes from a cylindrical shape to a flattened part, starting approximately at a distance from the handle head of one-fifth to one-sixth of the length of the handle. With a handle having a length of 130 mm, thus at about 105 mm from the end of the handle. The shape of the flattening is indicated by the section SB in FIG. 5. Preferably, the material of the handle is a titanium alloy.

Figure 6:
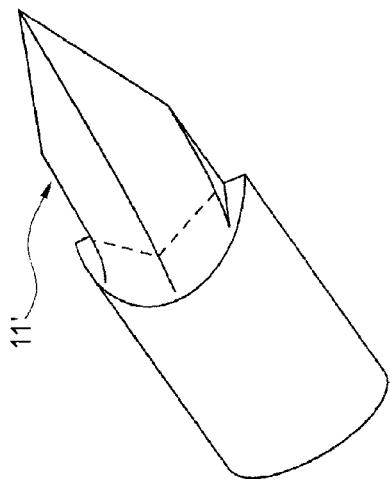
FIG. 6: a second blade form.

FIG. 6 shows a second embodiment of the top of the blade (16) with the cutting edges of the blade 11'. In this configuration, the cutting edges do not have a constant thickness. The edge where the cutting edges converge extends over the entire length of the blade and ends at the blade shank. The material of the blade 11' shown in FIG. 6 is thicker, which makes the blade more break-resistant. Although this is not especially clear from FIG. 6, the surfaces of the cutting edges end in a rounded area at the transition from the blade 11' to the blade shank (comparable to FIG. 2). The rounded areas have a radius that is prescribed by the contour of the grinding disk employed.

List of Reference Numerals
10, 10'blade
11, 11'blade face, second face shape
12 blade shank
14 rear surface

15 rear of the blade shank
16 top of the blade
18.1, 18.2 left, right cutting edges
20 angle of the bevel
22 angle of the equilateral triangle
24 diameter
25 cylinder axis
M mid-point of the cylinder
R radius of the blade shank
R1 rounded area
W angle
40 handle
41 handle head
42 diameter (envelope) on handle head
44 opening, bore (round or square)
45 first slanted surface (wedge)
46 second slanted surface
47 edge
49 flattening
48 angle slant of the first surface relative to axis handle
50 envelope
SA section near handle head
SB section near handle end (with flattening)

The invention claimed is:

1. A scalpel comprising a handle having a longitudinal axis and a handle head and a blade, the blade comprising a blade shank and a blade face with at least one cutting edge formed on the blade face and the blade being inserted into the handle head
wherein
the blade shank is configured together with the blade face as a body on which a continuous smooth rear surface is formed,
a front of the body opposite from the rear surface forms a cylindrical surface in the area of the blade shank and forms a top of the blade in the area of the blade face,
an end of the handle head has first and second surfaces that are slanted with respect to each other and that abut in an edge that is perpendicular to the axis of the handle, and
in a first of the slanted surfaces, there is an opening for inserting the blade, whereby the inserted blade lies in the opening in such a way that the smooth rear surface is flush with the first slanted surface.

2. The scalpel according to claim 1, wherein the blade shank is a cylindrical that is bisected parallel to a longitudinal axis of the body, which has its intersecting plane in the longitudinal axis of the body.

3. The scalpel according to claim 1, wherein a length of the blade is dimensioned in such a way that the blade remains within an imaginary envelope that extends beyond the end of the handle head.

4. The scalpel according to claim 1, wherein the first slanted surface on the handle head is slanted by an angle between 25° and 35° relative to the longitudinal axis of the handle.

5. The scalpel according to claim 1, wherein two cutting edges are formed on the blade.

6. The scalpel according to claim 1, wherein the cutting edges of the blade converge in the form of an equilateral triangle symmetrically relative to the longitudinal axis of the blade.

7. The scalpel according claim 1, wherein the shape of the equilateral triangle tapers at an angle of 45°.

8. The scalpel according claim 1, wherein the cutting edges are beveled from the rear surface towards the top of the blade.

9. The scalpel according to claim 1, wherein the blade is made of ceramic.

10. scalpel according to claim 1, wherein the blade is glued into the handle head.

11. The scalpel according to claim 1, wherein the first slanted surface on the handle head is slanted by an angle of 30° relative to the longitudinal axis of the handle.

* * * * *